United States Patent [19]

Thompson

[11] Patent Number: 5,010,899
[45] Date of Patent: Apr. 30, 1991

[54] SURGICAL DRAPE WITH LOOPS

[75] Inventor: Joseph F. Thompson, Lindenhurst, Ill.

[73] Assignee: Baxter International Inc., Deerfield, Ill.

[21] Appl. No.: 543,638

[22] Filed: Jun. 26, 1990

[51] Int. Cl.$^5$ .................. A61B 19/08; A61B 19/10
[52] U.S. Cl. ..................... 128/849; 128/852; 128/853
[58] Field of Search ............. 128/849, 850, 851, 852, 128/853, 854, 855, 856

[56] References Cited

U.S. PATENT DOCUMENTS

| Re. 27,710 | 7/1973 | Melges | 128/852 |
| 3,916,887 | 11/1975 | Kelly | 128/851 |
| 4,476,860 | 11/1984 | Collins et al. | 128/853 |
| 4,664,103 | 5/1987 | Martin et al. | 128/853 X |
| 4,899,762 | 2/1990 | Muller | 128/850 |

Primary Examiner—Robert A. Hafer
Assistant Examiner—Brian E. Hanlon
Attorney, Agent, or Firm—Kay H. Pierce; Paul C. Flattery

[57] ABSTRACT

A surgical drape for covering a patient during a procedure is described. The drape includes a plurality of loops that are attached to the upper surface of the drape for maintaining medical devices during the procedure. In the preferred embodiment, the loops are formed of a polymeric material and are attached to the drape in close proximity to a surgical site.

3 Claims, 3 Drawing Sheets

SURGICAL DRAPE WITH LOOPS

BACKGROUND OF THE INVENTION

The invention generally relates to surgical drapes and more specifically relates to drapes having means for maintaining medical devices in position during a surgical procedure.

During a surgical procedure, it is frequently desirable to have a system for holding surgical devices such as tubes, sponges, clamps, suction tips and ring instruments in position next to a patient. Typically, a patient is covered with a surgical drape during the procedure. A number of methods currently exists to attach or maintain medical devices on the drape during the procedure. For instance, one currently used method is to clamp a medical device onto the outer surface of the drape using towel clamps. Other methods include suturing or stapling devices to the drape and/or to the patient.

In the past, various drapes have been specifically designed to assist the medical staff in maintaining medical devices in position during a procedure. Some designs include troughs or pockets which extend along the side of a fenestration. A tube may be threaded through the trough or pocket. One disadvantage of such a design is the difficulty in threading the tube through the trough. Another disadvantage of such a design is that a trough provides very limited access to the patient. In other words, since medical devices may generally only be threaded through the ends of the trough, it is generally not possible to vary the location at which medical devices are positioned. One past technique used to overcome this disadvantage is to literally cut openings in the trough during the procedure to create additional access sites. This technique is somewhat cumbersome and is undesirable because lint or pieces of drape may be brought inadvertently in contact with the incision site and thereby cause postoperative complications.

Another drape specifically designed for the purpose of holding medical devices includes tabs formed of a nonwoven material which contain at least one hole in the tab through which the device may be threaded. Such tabs are generally known in the industries as "cord-holding tabs." Although such tabs may be useful in some circumstances, in situations in which the medical device is relatively heavy, or may be subjected to stress, the tabs may tear. If the tab tears, the medical device may slip and impair its ability to perform its intended function.

A relatively recent design for maintaining medical equipment involves the use of a pouch. In such cases, the pouch is generally located in close proximity to an incision site. The pouch may include various means to adjust its shape. For instance, the pouch may be formed from a single sheet of material and include an adhesive strip along two opposing edges. The sheet may be folded upon itself and sealed along its edges to form the pouch. Medical personnel may place a device along the length of the sheet, then fold the sheet and seal it along its edges to maintain the device in position. Similar to the disadvantages discussed above with respect to the trough design, a drape having such a pouch is limited in its usefulness because medical devices can only enter and exit the pouch at its ends.

It is therefore an object of the subject invention to provide a device for maintaining medical devices during a procedure which is relatively versatile with regard to placement of the devices.

It is another object of the invention to provide a device for maintaining medical instruments securely in position and in close proximity to a surgical site.

It is yet another object of the invention to provide a surgical drape which is relatively simple and low cost to manufacture.

It is also an object of the invention to provide a surgical drape having medical device maintaining means which is relatively simple and straight forward for medical personnel to use.

These and other objects of the subject invention will be more readily understood based on following description of the invention.

SUMMARY OF THE INVENTION

The invention can be briefly described as a container for use during a procedure. The container includes a containment sheet for positioning near a procedure. The container also includes a plurality of loops attached to a surface of the containment sheet for maintaining medical devices.

In one embodiment of the invention, a drape is provided for covering a patient during a procedure. The drape includes a main sheet for covering the operative site of the patient. The main sheet has an upper surface which is positioned away from the patient. The main sheet also has a lower surface positioned in proximity with the patient. The main sheet may include a fenestration means for accessing an operative site on the patient. A plurality of loops are provided which are attached to the upper surface of the main sheet for maintaining medical devices.

A BRIEF DESCRIPTION OF THE DRAWINGS

DETAILED DESCRIPTION OF THE PREFERRED EMBODIMENT

Figure 1:
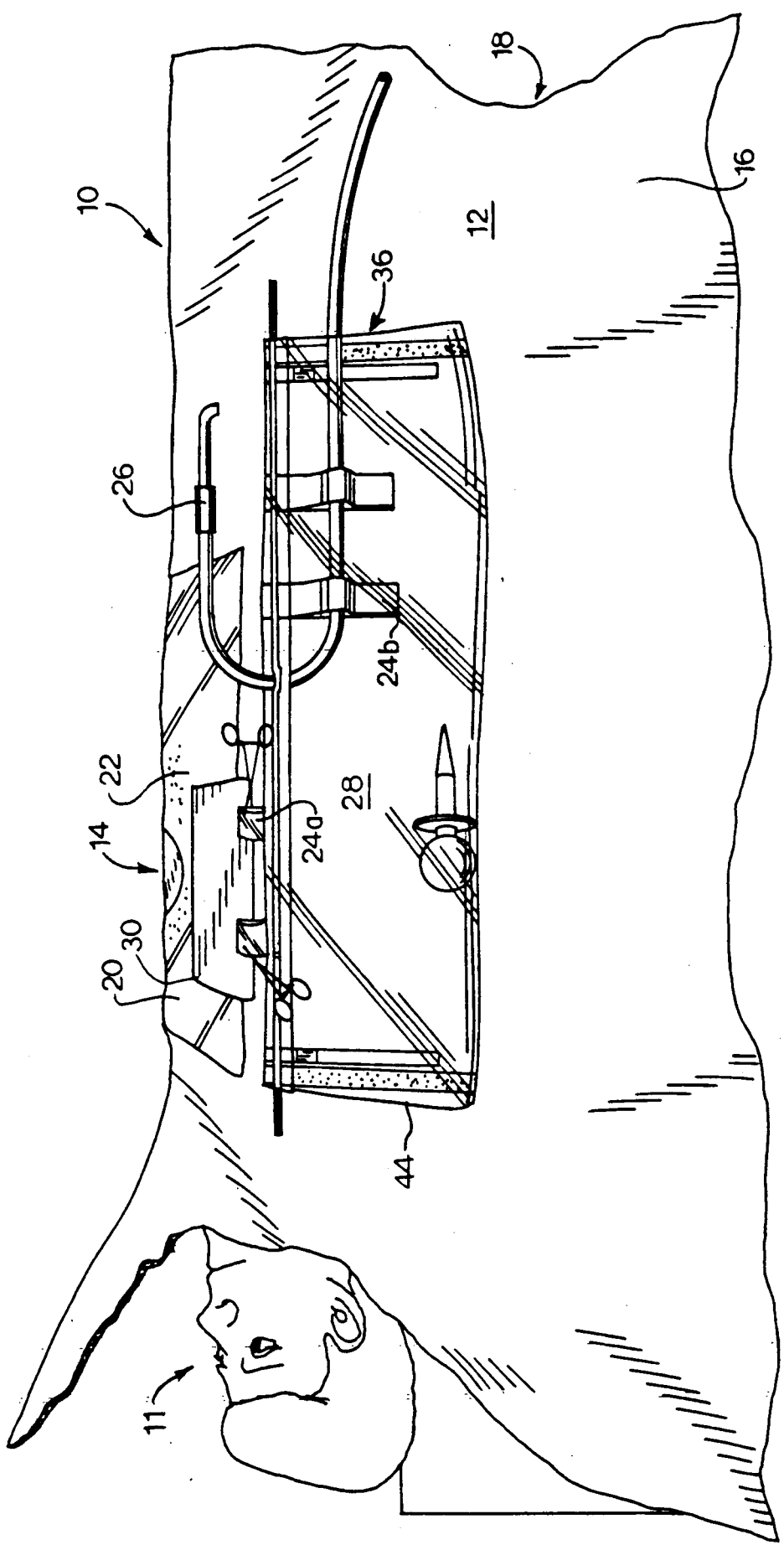
FIG. 1 is a perspective drawing of one embodiment of the subject invention.

Referring now to FIG. 1, a drape 10 for covering a patient 11 is described. The drape includes a main sheet 12 for covering the operative site 14 of a patient. The main sheet 12 includes an upper surface 16 which is positioned away from the patient. The main sheet also includes a lower surface 18 in proximity with the patient. The main sheet 12 generally includes a fenestration means 20 for accessing the operative site 14.

The fenestration means may be simply a hole in the drape or a layer of transparent polymeric film 22 with a pressure-sensitive adhesive attached to the lower surface of the film. The adhesive can be used to attach the film 22 to a patient at the operative site 14. A surgeon can create an opening in the film with a scalpel to access the operative site. One film commonly used in the industry for a fenestration means is generally referred to as incise film. One example of an incise film is Steri-Drape ® film which is manufactured by Minnesota Mining and Manufacturing Company.

In one embodiment of the invention, a plurality of loops 24 are attached to the upper surface 16 of the main sheet 12. A purpose of the loops is to provide a means for maintaining medical devices 26 in position during a surgical procedure.

In one embodiment of the invention, a second sheet 28 is provided. The second sheet 28 has edges, at least one edge 30 is attached to the upper surface 16 of the drape 10. The second sheet 28 may serve several purposes. First, the sheet may be formed of a liquid resistant or liquid impervious material to prevent seepage from the operative site back onto the patient. Second, the sheet may prevent fluid flow from the patient to the surgical staff or surrounding area. Third, as discussed in more detail below with respect to FIG. 3, the sheet may be used to assist the loops 24 in maintaining medical devices 26 in position. In one of the preferred embodiments of the invention, one edge 30 of the sheet 28 is attached to the upper surface 16 of the drape 10 in juxtaposition with the fenestration means 20. This method of attaching of the second sheet to the main sheet 12 allows the second sheet to perform the first two functions described above.

In one preferred embodiment, the loops 24 are located in close proximity to the attached edge 30 of the second sheet 28. It is desirable that the loops be formed from a material having a sufficient tensile strength to maintain the medical devices 26 in position during a procedure. It is also desirable that the loops be formed of a material that does not generally stretch when subjected to stress in order to ensure that the medical devices do not slip out of position as a medical procedure progresses. Although the loops 26 may be formed from a variety of materials, in the preferred embodiments, the loops are formed from polyethylene, polypropylene, polyester or polyvinyl films. Also, any combinations of the previously mentioned film materials may be used to form the loops.

In the preferred embodiment, the material used to form the second sheet 28 is the same material that is used to form the loops. If a second sheet is not provided in the drape, the loops may be formed from the same material that is used to form the drape. When a second sheet is provided, and the material used to form the second sheet and loops are the same, the loops may typically be thermally sealed to the second sheet. Thermal sealing may include either heat sealing or ultrasonic sealing of the loops to the second sheet.

Figure 2:
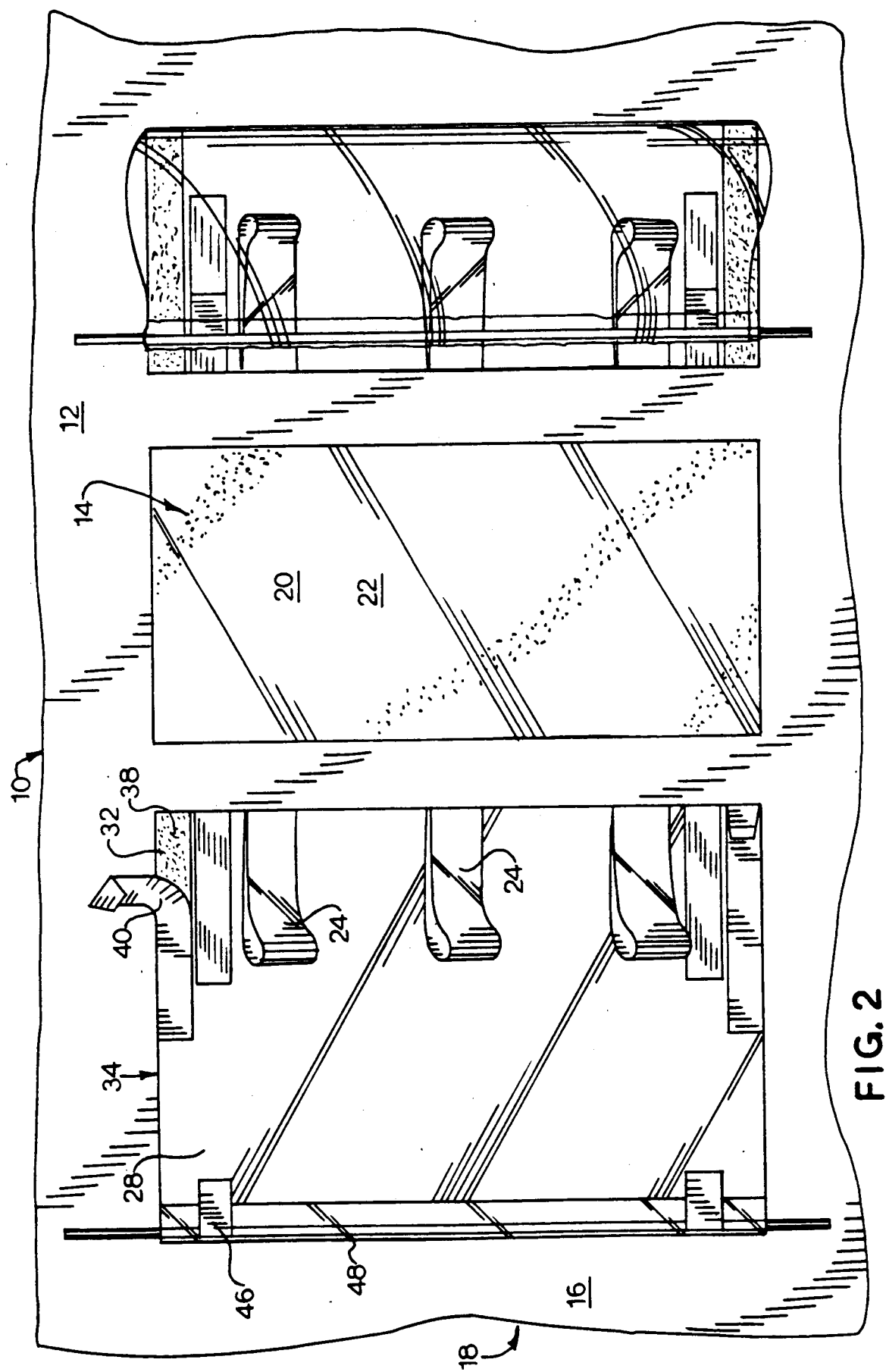
FIG. 2 is a front view of one embodiment of the invention.

As illustrated in FIG. 2, in one embodiment of the invention, a sealing means 32 may be provided along at least one edge 34 adjacent the attached edge 30. The purpose of the sealing means 32 is to allow the second sheet to be folded upon itself and sealed along the adjacent edge 34 to form a "pocket-like" structure 36. In this embodiment, the loops 24 may be positioned either inside or outside of the pocket-like structure as illustrated by elements 24a and 24b in FIG. 1. This embodiment, one method of providing a sealing means along edge 34 is to provide an adhesive tape 38 which is covered with release paper 40 which may be peeled away by the medical staff immediately prior to folding the second sheet 28 to form the pocket 36. In a preferred embodiment of the invention, the adhesive tape 38 is provided at opposite edges 34, 42 of the second sheet adjacent the attached edge 30 to allow the medical staff to form a trough 44 of variable size depending on the size of the medical devices 26 to be maintained.

Figure 3:
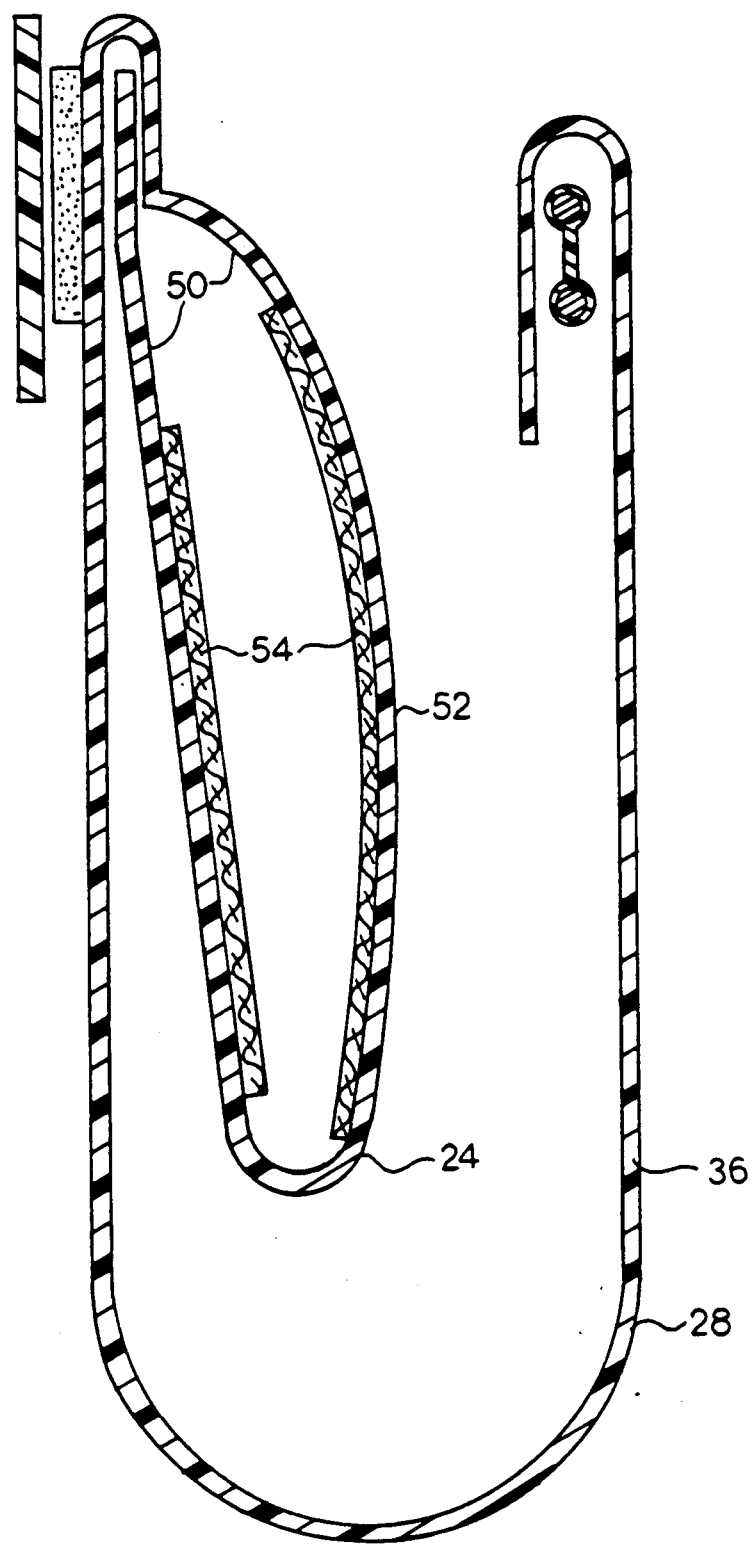
FIG. 3 is a side view of one embodiment of the invention.

Referring now to FIG. 3, when the length of the loops 24 is generally one-half the depth of a pocket 36 which is formed by folding the second sheet 28 onto itself, the second sheet will assist loops 24 in maintaining the medical devices 26 in position.

In another embodiment of the invention, as illustrated in FIG. 2, the second sheet 28 and the main sheet 12 may include fastening means 46 for fastening one edge 48 of the second sheet opposite the attached edge 30 to the main sheet in close proximity to the fenestration means 20. The purpose of the fastening means is to allow the second sheet 28 to be selectively formed into a tube-like structure in which the loops may be alternatively positioned either inside or outside to the tube-like structure. In the preferred embodiment incorporating a fastening means, the fastening means is formed from a hook and loop fastening system such as a Velcro ® material which is registered trademark of Velcro USA Corporation. The use of a fastening means along various portions of the second sheet together with the use of a plurality of loops 24 provides the medical staff with a tremendous amount of flexibility in positioning and maintaining medical devices 26 along an operative site.

In yet another embodiment of the invention as illustrated in FIG. 3, each loops 24 may be have an inner surface 50 and an outer surface 52. In this embodiment of the invention, the inner surface 50 may include a securing means 54 for adjustably closing a portion of the loop 24 onto a medical device 26. By way of example, the securing means 54 may be an adhesive or hook and loop fastening system.

I claim:

1. A drape for covering a patient during a procedure comprising:

a main sheet for covering the operative site of a patient, said main sheet having an upper surface positioned away from said patient and a lower surface positioned in proximity with said patient, said main sheet having fenestration means for accessing the operative site;

a plurality of loops attached to said upper surface of said main sheet for maintaining medical devices; and a second sheet having edges, one of said edges of said second sheet being attached to said upper surface of said drape in juxtaposition with said fenestration means, and said plurality of loops being located in close proximity to said attached edge of said second sheet, wherein said second sheet further includes sealing means along at least one edge adjacent said attached edge for allowing said second sheet to be foldingly sealed to itself along said adjacent edge to form a pocket-like structure, said loops being alternatively positioned inside or outside of said pocket-like structure.

2. A drape as set forth in claim 1 wherein said second sheet and said loops are formed from a polymeric material and said loops are thermally sealed to said second sheet.

3. A drape as set forth in claim 1 wherein said main sheet and said second sheet include:

fastening means for fastening an edge of said second sheet opposite said attached edge to said main sheet in close proximity to said fenestration means to allow said second sheet to selectively form a tube-like structure in which the loops may be alternatively positioned inside or outside of said tube-like structure.

* * * * *